US007001893B2

(12) United States Patent
Rao et al.

(10) Patent No.: US 7,001,893 B2
(45) Date of Patent: Feb. 21, 2006

(54) INCLUSION COMPLEX OF RIFAMPICIN, AN ANTI-TUBERCULAR DRUG, WITH β-CYCLODEXTRIN OR 2-HYDROXYPROPYL β-CYCLODEXTRIN AND A PROCESS THEREOF

(75) Inventors: Kakulapati Rama Rao, Andra Pradesh (IN); Nanduri Bhanumathi, Andra Pradesh (IN); Jhillu Singh Yadav, Andra Pradesh (IN); Neelam Srilakshmi Krishnaveni, Andra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/281,533

(22) Filed: Oct. 28, 2002

(65) Prior Publication Data

US 2004/0082541 A1    Apr. 29, 2004

(51) Int. Cl.
*A61K 31/724* (2006.01)
*C08B 37/16* (2006.01)
(52) U.S. Cl. .................. 514/58; 514/60; 514/338; 514/26; 536/103; 536/120; 536/122; 536/46; 424/96; 435/473
(58) Field of Classification Search .................. 514/58, 514/60, 338, 26; 536/103, 120, 122, 46; 424/440, 443, 500, 400; 426/96; 435/473
See application file for complete search history.

(56) References Cited

U.S. PATENT DOCUMENTS 5,134,127 A * 7/1992 Stella et al. ................... 514/58
6,495,160 B1 * 12/2002 Esposito et al. ............. 424/451
6,500,463 B1 * 12/2002 van Lengerich ............ 424/499

FOREIGN PATENT DOCUMENTS

CN        1080528      * 1/1994

OTHER PUBLICATIONS

Kuchekar et al. "Solid dispersions of rifampicin." Abstract: Eastern Pharmacist, 1998, 41(492), 133-134.*
Singh, Saranjit, "Study on poor bioavailability of rifampicin in FDCs for anti-TB therapy," NIPER-Chronicle Pharmabiz, Dec. 20, 2001, p. 28.
Kuchekar et al., "Solid Dispersions of Rifampicin," The Eastern Pharmacist, 1998, pp. 133-143.

* cited by examiner

*Primary Examiner*—James O. Wilson
*Assistant Examiner*—Devesh Khare
(74) *Attorney, Agent, or Firm*—Baker Botts LLP

(57) ABSTRACT

The present invention relates to an inclusion complex of Rifampicin and cyclodextrin (CD) that can be used as an anti-tubercular drug. The present invention also relates to a process for synthesizing inclusion complexes of the anti-tubercular drug, Rifampicin, with β-CD (β-cyclodextrin) and HP-β-CD (2-hydroxy propyl cyclodextrin) and characterization of these inclusion complexes.

14 Claims, 2 Drawing Sheets

R = H; β−Cyclodextrin
R = 2-Hydroxypropyl;
    2-Hydroxy propyl-
    β−Cyclodextrin R = H; β–Cyclodextrin
R = 2-Hydroxypropyl;
    2-Hydroxy propyl-
    β–Cyclodextrin

RIFAMPICIN

INCLUSION COMPLEX OF RIFAMPICIN, AN ANTI-TUBERCULAR DRUG, WITH β-CYCLODEXTRIN OR 2-HYDROXYPROPYL β-CYCLODEXTRIN AND A PROCESS THEREOF

BACKGROUND OF INVENTION

The present invention relates to an inclusion complex comprising Rifampicin and cyclodextrin useful as drug in tuberculosis. The present invention also relates to synthesis of Rifampicin-cyclodextrin inclusion complexes, which find use in tuberculosis therapy as drug delivery systems.

Rifampicin is an international nonproprietary name. Other names used are Rifamycin AMP, Rifampin and Rifaldazine. Rifampicin is designated by IUPAC rules as 2,7-(epoxy pentadeca[1,11,13]trienimino)naphtho[2,1-b]furan1,11 (2H)-dione5,6,9,17,19,21-hexa hydroxy-23-methoxy-2,4,12,16,18,20,22-hepta methyl-8-[N-(4-methyl-1-piperazinyl) formimidoyl]-21-acetate. Rifampicin is a commonly used anti-mycobacterial drug for the treatment of tuberculosis. The chemical structure of Rifampicin is shown in FIG. 2.

Cyclodextrins (CDs) are cyclic oligosaccharides possessing hydrophobic cavities. CDs can be used in combination with various drugs either for complexation or as auxiliaries such as diluents, solubilizers or tablet ingredients (*Comprehensive Supramolecular Chemistry*, Vol 3, Szejtli J, Osa T, Pergamon, UK, 1996). The advantage of using CDs mainly comes from their inclusion complex formation. The complexation can protect the molecule and can eventually have considerable pharmaceutical potential.

There are various advantages for drug delivery using inclusion complex formation. Incompatible drugs can be mixed when one of them is complexed with CDs. The release rate of drugs can be controlled. The solubility of water insoluble drugs can be improved. The instability of drugs in water and the acidic environment of the stomach conditions can be improved, since the rate of hydrolysis, photo-decomposition, auto-catalytic reactions etc., are considerably reduced. Furthermore, percutaneous or rectal absorption can be improved by the enhanced release of drugs from ointments or suppository bases. Thus, CD inclusion complexes of drugs have several advantages.

The inclusion complex formation can be characterized by powder X-ray diffraction patterns and IR spectroscopy (*Comprehensive Supramolecular Chemistry*, Vol 3, Szejtli J, Osa T, Pergamon, UK, 1996).

A recent publication has reported the impaired bioavailability of Rifampicin in the presence of Isoniazid, an anti-mycobacterial drug also used in treatment of tuberculosis, in fixed dose combinations (FDCs) due to the decomposition of Rifampicin in the stomach (*Chronicle Pharmabiz*, p. 28, Dec. 20, 2001). The acidic environment of the stomach causes Rifampicin to be hydrolyzed to an insoluble, less absorbable form. Thus, there is a need for a formulation that protects Rifampicin from degradation in the acidic environment of the stomach.

The present invention contemplates a Rifampicin and β-cyclodextrin containing inclusion complex that may be used in the treatment of tuberculosis. This formulation is also potentially advantageous since stability and release can be controlled. Combinations of Rifampicin and cyclodextrin formulations reported so far are only dispersions of Rifampicin and cyclodextrin (East. Pharm., p. 133, vol. 41(492), 1998), that have not been isolated and characterized inclusion complexes containing Rifampicin and cyclodextrin.

Accordingly, studies were undertaken to make the inclusion complexes of Rifampicin with β-cyclodextrin (β-CD) and 2-hydroxypropyl-β-cyclodextrin (HP-β-CD).

SUMMARY OF THE INVENTION

The present invention relates to an inclusion complex of Rifampicin with cyclodextrin (CD) that can be used as an anti-tubercular drug. The present invention also relates to a process for synthesizing inclusion complexes of the anti-tubercular drug, Rifampicin, with β-CD (β-cyclodextrin) and HP-β-CD (2-hydroxy propyl cyclodextrin) and characterization of these inclusion complexes. In addition, a further aspect of the invention is to provide a general process for preparing inclusion complexes of cyclodextrin with large size molecules.

DETAILED DESCRIPTION OF THE INVENTION

The present invention provides an inclusion complex of Rifampicin with cyclodextrin as an anti-tubercular drug.

One embodiment of the invention provides an inclusion complex, wherein the cyclodextrin used is selected from β-cyclodextrin and 2-hydroxy propyl cyclodextrin.

The inclusion complex enhances the bioavailability and solubility of the drug Rifampicin.

The inclusion complex and the drug exist in an encapsulated form can lead to controlled release of the drug.

Fixed dose combination (FDC) formulations facilitate treatment of tuberculosis since the correct number of drugs in the correct dosages are combined in a single tablet. The inclusion complex of the present invention provides a new approach to anti-tuberculosis therapy containing fixed dose combination.

The inclusion complex is characterized by X-ray diffraction and infrared studies as shown in the Examples section.

The encapsulation of the drug under solid conditions is achieved to enhance bioavailability and solubility.

β-cyclodextrin (β-CD) is a cyclic oligosaccharide consisting of seven glucose units, with 2-Hydroxypropyl-α-cyclodextrin (HP-β-CD) being a β-cyclodextrin molecule substituted with a hydroxypropyl group at the 2-position of the glucose. HP-β-CD has also been used as a drug carrier due to its low toxicity, high tolerance and excellent solubilizing and stabilizing abilities. HP-β-CD has generally been found to be safe and no adverse effects were observed in human studies. (*Comprehensive Supramolecular Chemistry*, Vol 3, Szejtli J, Osa T, Pergamon, UK, 1996).

Figure 1:
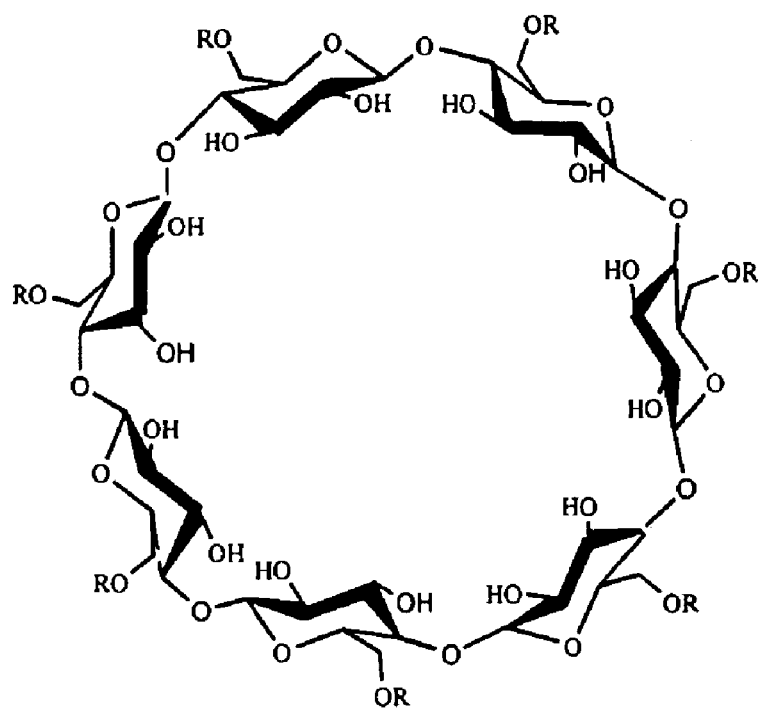
FIG. 1 shows the chemical structures of β-cyclodextrin (β-CD) and (2-Hydroxypropyl)-β-cyclodextrin (HP-β-CD).
Figure 2:
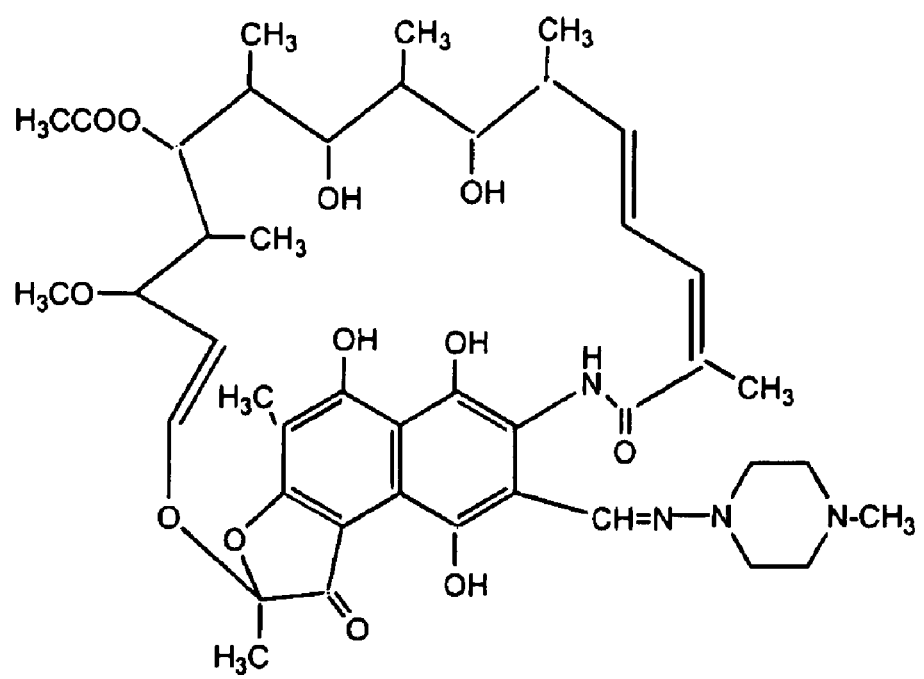
FIG. 2 shows the chemical structure of Rifampicin.

The cyclodextrins (FIG. 1) are cyclic oligosaccharides possessing hydrophobic cavities and mimic enzymes in their capability to bind substrates selectively and catalyze chemical reactions. β-Cyclodextrin consists of seven glucose units linked by α-1,4 glycosidic bonds into a macrocycle with a hydrophobic cavity. HP-β-CD is a substituted β-CD at 2-position with a 2-hydroxy propyl group. Each cyclodextrin has its own ability to form inclusion complexes with specific guests into the hydrophobic cyclodextrin cavity. The most important pharmaceutical application of cyclodextrins is to enhance the solubility and bioavailability of drug molecules.

In another embodiment, the present invention provides a process for preparation of inclusion complexes of Rifampicin with β-cyclodextrin, the process comprising adding Rifampicin to cyclodextrin and grinding in an agate mortar to form an uniform powdery material of Rifampicin-dextrin inclusion complex.

The process for the preparation of inclusion complexes of Rifampicin with β-cyclodextrin (β-CD) or 2-Hydroxypropyl β-cyclodextrin (HP-β-CD) which comprises a phenomenon of converting a free drug into an encapsulated form under solid state conditions. The formation of cyclodextrin complexes with Rifampicin may be with β-CD or HP-β-CD.

The Examples show a process for the synthesis of inclusion complexes of the anti-tubercular drug, Rifampicin with β-cyclodextrin (β-CD) or 2-hydroxypropyl-β-cyclodextrin (HP-β-CD), which has been achieved for the first time.

The inclusion complexes of the anti-tubercular drug Rifampicin with cyclodextrins were prepared by adding Rifampicin in equimolar ratio to the respective cyclodextrins and intimately grinding the mixture using mortar and pestle for varying reaction times ranging from five to eight hours.

Accordingly, the present invention deals with the synthesis of inclusion complexes of the anti-tubercular drug, Rifampicin with β-CD or HP-β-CD. The synthesis of each compound perse is known in the art.

The compounds of the present invention contemplate a formulation for Rifampicin which is more stable and has considerable pharmaceutical potential. Incorporation of Rifampicin into an inclusion complex also allows for greater control over the drug release rate in the subject. There is also a possibility of improving the stability of Rifampicin in fixed dose combinations (FDCs). This invention may provide a new approach to anti-tuberculosis therapy containing FDCs.

EXAMPLES

The following examples are given by way of illustration and therefore should not construe the limit of the scope of the present invention.

Example 1

Rifampicin-β-cyclodextrin Inclusion Complex

The cyclodextrin inclusion complex was prepared by the grinding method under solid state conditions. β-Cyclodextrin (13.79 g) was taken in an agate mortar and Rifampicin (10 g) was added while mixing intimately. The ingredients were continuously ground ranging from 5–8 hrs to form a uniform powdery material. The inclusion complex of "Rifampicin" with β-cyclodextrin thus formed has been characterized by the powder X-ray diffraction patterns and IR spectral data. The inclusion complex has been identified by comparing its X-ray and IR spectral data with Rifampicin and β-CD.

Powder X-ray Studies:

The Powder X-ray Diffractometer, Siemens/D-5000 was used to conduct Powder X-ray studies. The powder X-ray diffractograms were measured in 2θ angles.

The most significant measurements are as follows:
β-CD:
   4.3, 6.2, 8.9, 10.4, 12.6, 18.8, 22.6, 27.0, 35.2
Rifampicin:
   7.8, 9.5, 10.9, 12.6, 15.8, 16.9, 19.6, 21.3, 26.0
Rifampicin-β-cyclodextrin complex (Rif-β-CD):
   4.3, 8.7, 10.6, 12.6, 15.7, 18.8, 25.5, 35.2, 46.4.

In the inclusion complex, some significant peaks are either shifted, disappeared or some new peaks have appeared. The peaks at 18.8 and 22.6 in β-CD have disappeared in the complex. The peaks at 4.3, 12.6 and 27.0 in β-CD have been reduced in intensity in the complex. The new peaks that appeared in the complex are at 18.6, 25.5 and 46.4

The following peaks of Rifampicin that disappeared in the complex are 9.5, 10.9, 19.6 and 26.0. The significant peaks of Rifampicin at 12.6, 15.8, 16.9 and 21.3 are reduced in intensity.

Infrared Spectral Studies:

The infrared spectral studies were conducted on the Perkin Elmer Spectrum RX/Ft IR system 500–3500 $cm^{-1}$.

The IR spectra of the drug Rifampicin complex with β-CD and also the individual drug Rifampicin have been recorded as KBr pellets.

The inclusion complex formation has also been proved by IR spectroscopy. Bands due to the included part of the guest molecule have shifted or their intensities altered. The acetoxyl C=O vibration at 1728.2 $cm^{-1}$ and carbonyl C=O absorption at 1730.4 $cm^{-1}$ of Rifampicin have been shifted to lower frequency and appear as single peak at 1722.2 $cm^{-1}$ where as the amide NH—C=O shows only a minor shift from 1651.2 $cm^{-1}$ to 1647.8 $cm^{-1}$. However, only a small shift was observed for C=C vibration from 1566.4 $cm^{-1}$ in the drug to 1565.1 $cm^{-1}$ in the complex. This clearly indicates the formation of inclusion complex of Rifampicin with β-CD.

Example 2

Rifampicin-2-hydroxypropyl-β-cyclodextrin Inclusion Complex

To Rifampicin (10 g) in an agate mortar, 2-hydroxypropyl-β-cyclodextrin (16.77 g) was added and ground well for periods ranging from 5 to 8 hrs to form an uniform powdery material. The inclusion complex of the drug thus formed was isolated and characterized.

Powder X-ray Studies

Rifampicin with 2-hydroxypropyl-β-cyclodextrin (HP-β-CD) complex has been confirmed by comparing its data of X-ray diffraction pattern with the parent drug and HP-β-CD.

The important peaks are shown hereunder.
2-HP-β-CD:
   4.8, 11.6, 17.4, 19.1, 23.1, 29.1, 33.0, 35.0, 39.9
Rifampicin-2-hydroxy propyl-β-cyclodextrin inclusion complex (Rif-2HP-β-CD):
   1.4, 5.9, 12.8, 14.2, 16.3, 18.2, 21.4, 25.8, 30.6 and 31.8

Comparison of the data of the complex with Rifampicin and HP-β-CD are as follows. The following peaks of Rifampicin at 7.8, 9.5 and 10.9 have disappeared in the complex. The peak at 21.3 was reduced in intensity as compared to Rifampicin. As compared to HP-β-CD, new peaks have appeared at 14.2, 25.8 and disappearance of the peaks at 4.8 and 11.6 was observed. The peak at 23.1 was reduced in intensity.

Thus the difference in the X-ray diffraction patterns of the inclusion complexes of the drug Rifampicin with β-CD and HP-β-CD and that of the individual components by the appearance of new peaks, disappearance of some peaks and also reduction in intensity of some more peaks as described above clearly indicates the formation of inclusion complex of Rifampicin with β-CD and HP-β-CD.

Infrared Spectral Studies

Infrared spectral studies have also been carried out to confirm the formation of inclusion complex.

The IR spectrum of RIF-HP-β-CD complex shows the merging of the acetoxyl C═O at 1728.2 cm$^{-1}$ and carbonyl C═O absorption at 1730.4 cm$^{-1}$ of Rifampicin to give a single peak at a lower frequency 1719.8 cm$^{-1}$, whereas the amide NH—C═O absorption of Rifampicin at 1651.2 cm$^{-1}$ shifts to a lower frequency at 1648.4 cm$^{-1}$. A significant shift in C═C absorption band from 1566.4 cm$^{-1}$ to 1562.8 cm$^{-1}$ has also been observed. This data clearly indicates the formation of inclusion complex of Rifampicin with HP-β-CD.

We claim:

1. An inclusion complex of Rifampicin and cyclodextrin with an X-ray diffraction profile where there are peaks at about 18.6, 25.5 and 46.4.

2. An anti-tubercular drug comprising the inclusion complex of Rifampicin and cyclodextrin of claim 1 and a carrier.

3. The anti-tubercular drug of claim 2, wherein the cyclodextrin is selected from the group consisting of β-cyclodextrin and 2-hydroxy propyl cyclodextrin.

4. The anti-tubercular drug of claim 2, wherein the complex has enhanced bioavailability and solubility of Rifampicin.

5. The anti-tubercular drug of claim 2, wherein the drug is encapsulated in solid form.

6. The inclusion complex of claim 1, wherein the cyclodextrin is β-cyclodextrin.

7. The inclusion complex of claim 1, wherein the inclusion complex is in an encapsulated form.

8. A process for preparing inclusion complexes of Rifampicin and β-cyclodextrin, said process comprising adding Rifampicin to cyclodextrin and grinding in an agate mortar to form a uniform powdery material of Rifampicin-cyclodextrin inclusion complex wherein the complex has enhanced bioavailability and solubility of the drug Rifampicin, and the inclusion complex provides improved stability of Rifampicin in fixed dose combination.

9. The process of claim 8, wherein the cyclodextrin is selected from group consisting of β-cyclodextrin and 2-hydroxy propyl β-cyclodextrin.

10. The process of claim 8, wherein the Rifampicin-cyclodextrin inclusion complex is encapsulated in solid form.

11. An inclusion complex of Rifampicin and 2-hydroxy propyl β-cyclodextrin with an X-ray diffraction profile where there are peaks at about 14.2 and 25.8.

12. The inclusion complex of claim 11, wherein the inclusion complex is in an encapsulated form.

13. An anti-tubercular drug comprising the inclusion complex of Rifampicin and 2-hydroxy propyl β-cyclodextrin of claim 11 and a carrier.

14. The anti-tubercular drug of claim 13, wherein the drug is encapsulated in solid form.

* * * * *